United States Patent
Yasuma et al.

(10) Patent No.: US 6,355,672 B1
(45) Date of Patent: Mar. 12, 2002

(54) BENZOTHIEPIN DERIVATIVES, PROCESS FOR THE PREPARATION OF THE SAME AND USES THEREOF

(75) Inventors: Tsuneo Yasuma, Ibaraki; Haruhiko Makino, Hyogo; Akira Mori, Amagasaki, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/744,857

(22) PCT Filed: Aug. 6, 1999

(86) PCT No.: PCT/JP99/04269

§ 371 Date: Jan. 30, 2001

§ 102(e) Date: Jan. 30, 2001

(87) PCT Pub. No.: WO00/08018

PCT Pub. Date: Feb. 17, 2000

(30) Foreign Application Priority Data

Aug. 7, 1998 (JP) ............................... 10-225065

(51) Int. Cl.$^7$ ................ C07D 337/08; A61K 31/38; A61P 19/08

(52) U.S. Cl. .................. 514/431; 548/188; 548/196; 548/213; 548/227; 548/229; 548/243; 548/311.4; 548/311.7; 548/526; 548/527; 549/9; 544/60; 544/61; 544/62; 544/197; 544/202; 544/175; 514/336; 514/372; 514/376; 514/378; 514/380; 514/397; 514/228.2; 514/228.8; 514/232.8; 514/233.5; 514/96

(58) Field of Search ................. 548/188, 196, 548/213, 227, 229, 243, 311.7, 311.4, 526, 527; 549/9; 544/60, 61, 62, 197, 202, 175; 514/431, 336, 372, 376, 378, 380, 397, 228.2, 228.8, 232.8, 233.5, 96

(56) References Cited

U.S. PATENT DOCUMENTS

| | | | | |
|---|---|---|---|---|
| 5,071,841 A | 12/1991 | Sohda et al. | .............. | 514/96 |
| 5,158,943 A | 10/1992 | Sohda et al. | .............. | 514/96 |
| 5,952,512 A | 9/1999 | Maeda et al. | .............. | 549/12 |
| 6,190,695 B1 | 2/2001 | Hoshino et al. | .............. | 424/464 |

FOREIGN PATENT DOCUMENTS

| | | |
|---|---|---|
| EP | 0376197 | 7/1990 |
| EP | 0460488 | 12/1991 |
| EP | 0719782 | 7/1996 |
| JP | 8-231569 | * 8/1996 |
| WO | 86/01407 | * 3/1986 |
| WO | 94/13642 | * 6/1994 |
| WO | WO96/39134 | 12/1996 |
| WO | WO99/65474 | 12/1999 |

OTHER PUBLICATIONS

Ahluwalia, et al., 1986, Indian J. Chem., 25B(5), 502–4.*
Akiyama, et al. "TAK–778, a Novel Synthetic 3–Benzothiepin Derivative, promotes Chondrogenesis in Vitro and in Vivo" Biochemical and Biophysical Research Communications 261:131–138 (1999).

* cited by examiner

Primary Examiner—T. A. Solola
Assistant Examiner—Andrea D'Souza
(74) Attorney, Agent, or Firm—Mark Chao; Elaine M. Ramesh

(57) ABSTRACT

The invention provides compounds of the formula:

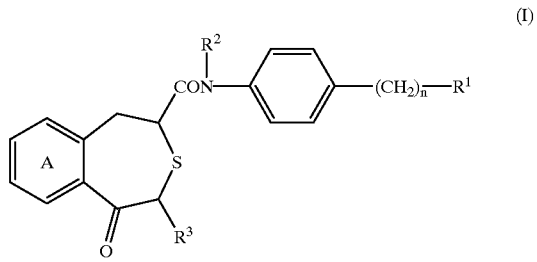

wherein the ring A is an optionally substituted benzene ring; $R^1$ is an optionally substituted non-aromatic heterocyclic group; $R^2$ and $R^3$ are independently hydrogen atom or an optionally substituted hydrocarbon group; n is an integer of 0–3; or salts thereof, which are useful as medicines having an osteogenesis promoting effect and chondrogensis promoting effect.

The present invention relates to an amine compound having an excellent effect of inhibiting production and/or secretion of amyloid-b protein, a production and use thereof. Especially, it is effective for preventing and/or treating, for example, neurodegenerative diseases, amyloid angiopathy, neurological disorders caused by cerebrovascular disorders, and so forth.

13 Claims, No Drawings

BENZOTHIEPIN DERIVATIVES, PROCESS FOR THE PREPARATION OF THE SAME AND USES THEREOF

This application is a 371 of application Ser. No. PCT/JP99/04269, filed on Aug. 6, 1999.

TECHNICAL FIELD

The present invention relates to benzothiepine derivatives having an osteogenesis promoting effect and a chondrogenesis promoting effect, to a process for producing the same, and to a pharmaceutical composition comprising the same as effective component.

BACKGROUND ART

Bone diseases are pathological states or disorders in which a certain symptom or risk occurs due to a decrease in bone quantity that has reached a certain level. For example, a major symptom of osteoporosis, one of the bone diseases, is kyphosis, and a fracture in dorsolumbar bone and vertebral centra, neck of the thigh bone, inferior extremity of radius, ribs, superior extremity of humerus, and the like. In osseous tissue, osteogenesis and destruction by bone resorption are repeated, while remaining balanced, and osteoblasts in osteogenesis and osteoclasts play a central role in bone resorption.

Loss of the balance between osteogenesis and destruction by bone resorption is accompanied by a decrease in quantity of the bone. Conventionally, as prophylactic or therapeutic agents, bone resorption-suppressing substances such as estrogens, calcitonins, bisphosphonates, and the like have primarily been used. However, these bone resorption suppressors fail to achieve a satisfactory effect in some cases, due to limitations of the subject or to uncertain efficacy.

So far it has been reported that benzothiepine derivatives have an osteogenesis promoting effect (Japanese Unexamined Patent Publication No. (hereinafter referred to as JP-A) 3-232880/1991; JP-A 4-364179/1992; JP-A 8-231569/1996).

It is desirable to develop more effective prophylactic or therapeutic agents for bone diseases and chondropathy which have an osteogenesis promoting effect and a chondrogenesis promoting effect and which have excellent stability, absorption and bioavailability as oral preparations.

DISCLOSURE OF INVENTION

The present inventors synthesized a variety of benzothiepine derivatives and worked diligently to investigate the biological activity and pharmacological behavior of these derivatives. As a result, they discovered that compounds having a group of the formula:

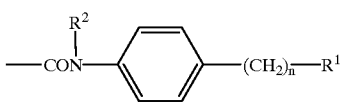

[wherein $R^1$ is an optionally substituted non-aromatic heterocyclic group; $R^2$ is a hydrogen atom or hydrocarbon group which may have a substituent] at the 2 position of benzothiepine structure exhibit an excellent osteogenesis promoting effect and a chondrogenesis promoting effect and are superior in oral absorption. The present inventors further investigated based on these findings and succeeded in establishing the present invention.

The present invention relates to:
(1) a compound (I) of the formula:

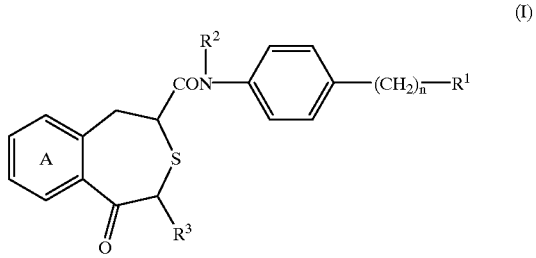

wherein the ring A is an optionally substituted benzene ring; $R^1$ is an optionally substituted non-aromatic heterocyclic group; $R^2$ and $R^3$ are independently hydrogen atom or an optionally substituted hydrocarbon group; n is an integer of 0–3; or a salt thereof, (2) a compound as described in the above item (1), wherein the ring A is a benzene ring which may be substituted by 1 or 2 substituents selected from the group consisting of halogen atom, hydroxy, $C_{1-10}$ alkyl, $C_{1-10}$ alkoxy, alkylenedioxy of the formula: —O—$(CH_2)m$—O— (wherein m is an integer of 1–4) and $C_{1-10}$ alkylthio; and $R^2$ and $R^3$ are independently hydrogen atom, $C_{1-6}$ alkyl or phenyl, (3) a compound as described in the above item (1), wherein the ring A is a group of the formula:

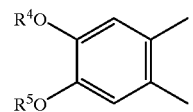

wherein $R^4$ and $R^5$ are independently hydrogen atom or $C_{1-10}$ alkyl or $R^4$ and $R^5$ may be bound to each other to form a $C_{1-4}$ alkylene chain; and $R^2$ and $R^3$ are independently hydrogen atom or $C_{1-6}$ alkyl, (4) a compound as described in the above item (1) or (3), wherein the non-aromatic heterocyclic group of the optionally substituted non-aromatic heterocyclic group represented by $R^1$ is a 5- to 6-membered non-aromatic heterocyclic group containing from 1 to 4 heteroatoms selected from the group consisting of nitrogen atom, sulfur atom and oxygen atom, (5) a compound as described in the above item (4), wherein the 5- to 6-membered non-aromatic heterocyclic group is one containing at least 1 nitrogen atom, (6) a compound as described in the above item (5), wherein the heterocycle of the 5- to 6-membered non-aromatic heterocyclic group is pyrrolidine, imidazolidine, thiazolidine, isothiazolidine, oxazolidine, oxadiazolidine, piperidine, piperazine, thiomorpholine or morpholine, (7) a compound as described in the above item (1), wherein the substituent or substituents in the optionally substituted non-aromatic heterocyclic group represented by $R^1$ are 1–3 of halogen atom, hydroxy or oxo, $C_{1-10}$ alkyl, $C_{1-6}$ alkoxy, $C_{1-6}$ acyl, amino, mono- or di-$C_{1-6}$ alkylamino, $C_{1-6}$ alkylsulfonyl, carboxy or $C_{1-6}$ alkoxy-carbonyl, (8) a compound as described in the above item (3), wherein $R^2$ is a hydrogen atom; $R^3$ is $C_{1-3}$ alkyl; and $R^4$ and $R^5$ may be bound to each other to form a $C_{1-2}$ alkylene chain, (9) a compound as described in the above item (3), wherein $R^2$ and $R^3$ are independently a hydrogen atom, and $R^4$ and $R^5$ are independently a $C_{1-3}$ alkyl group,

(10) N-[4-(4-morpholinylmethyl)phenyl]-1,2,4,5-tetrahydro-7,8-methylenedioxy-4-methyl-5-oxo-3-benzothiepine-2-carboxamide,
N-[4-(2,4-dioxothiazolidin-5-ylmethyl)phenyl]-1,2,4,5-tetrahydro-7,8-methylenedioxy-4-methyl-5-oxo-3-benzothiepine-2-carboxamide, or
N-[4-(2,4-dioxo-oxazolidin-5-ylmethyl)phenyl]-1,2,4,5-tetrahydro-7,8-methylenedioxy-4-methyl-5-oxo-3-benzothiepine-2-carboxamide, or a salt thereof,

(11) an optically active compound of the formula:

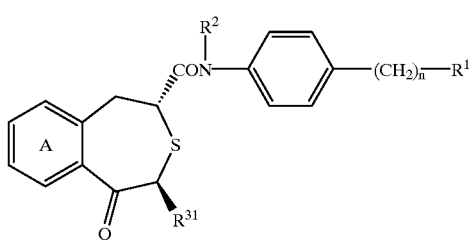

wherein the ring A is an optionally substituted benzene ring; $R^1$ is an optionally substituted non-aromatic heterocyclic group; $R^2$ is a hydrogen atom or an optionally substituted hydrocarbon group; $R^{31}$ is an optionally substituted hydrocarbon group; and n is an integer of 0–3; or a salt thereof,

(12) a process for producing a compound (I) of the formula:

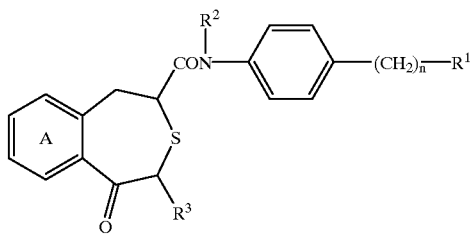

wherein the ring A is an optionally substituted benzene ring; $R^1$ is an optionally substituted non-aromatic heterocyclic group; $R^2$ and $R^3$ are independently a hydrogen atom or an optionally substituted hydrocarbon group; and n is an integer of 0–3; or a salt thereof, which comprises reacting a compound (II) of the formula:

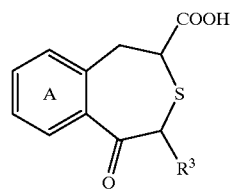

wherein each symbol has the same meanings as mentioned above; or a reactive derivative at the carboxy group thereof or a salt thereof, with a compound (III) of the formula:

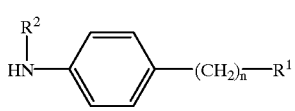

wherein each symbol has the same meanings as mentioned above; or a reactive derivative at the amino group thereof or a salt thereof,

(13) a compound (III') of the formula:

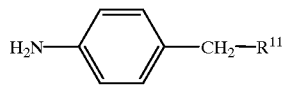

wherein $R^{11}$ is pyrrolidinyl, dioxopyrrolidinyl, piperidinyl, mono- or di-oxopiperidinyl, morpholinyl, thiomorpholinyl, thiazolidinyl, dioxothiazolidinyl, dioxoimidazolidinyl, 1-methyldioxoimidazolidinyl, dioxooxazolidinyl, dioxotetrahydroisothiazolidinyl, momo- or di-oxooxazolidinyl, or dioxooxadiazolidinyl; or a salt thereof,

(14) a prodrug or a salt thereof of the compound as described in the above item (1),

(15) a pharmaceutical composition which comprises a compound (I) of the formula:

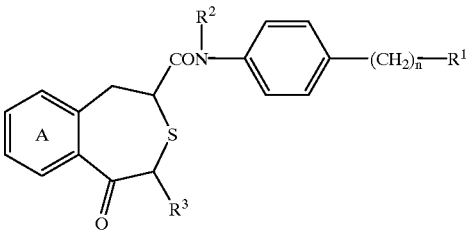

wherein the ring A is an optionally substituted benzene ring; $R^1$ is an optionally substituted non-aromatic heterocyclic group; $R^2$ and $R^3$ are independently hydrogen atom or an optionally substituted hydrocarbon group; and n is an integer of 0–3; or a salt thereof,

(16) a pharmaceutical composition according to the above item (15), which is an osteogenesis promoting agent,

(17) a pharmaceutical composition according to the above item (15), which is a prophylactic or therapeutic agent for bone diseases,

(18) a pharmaceutical composition according to the above item (15), which is a prophylactic or therapeutic agent for fracture, and

(19) a pharmaceutical composition according to the above item (15), which is a prophylactic or therapeutic agent for chondropathy.

In the above-mentioned formulae, as for the substituent on the optionally substituted benzene ring represented by the ring A, for example, halogen atom, hydroxy, nitro, optionally substituted alkyl group, optionally substituted hydroxy group, optionally substituted mercapto group, optionally substituted amino group, acyl group, mono- or di-alkoxyphosphoryl group, phosphono, optionally substituted aryl group, optionally substituted aralkyl group, or optionally substituted aromatic heterocyclic group may be used, and these may be the same or different, of which 1 to 4, preferably 1 or 2, may be substituted on the benzene ring.

The "halogen atom" includes, for example, fluorine, chlorine, bromine and iodine.

The alkyl group of the "optionally substituted alkyl group" includes, preferably, alkyl of 1–10 carbon atoms, e.g., methyl, ethyl, propyl, isopropyl, butyl, isobutyl, sec-butyl, tert-butyl, pentyl, isopentyl, neopentyl, hexyl, heptyl, octyl, nonyl, dodecyl, and the like, and cycloalkyl of 3–7 carbon atoms, e.g., cyclopropyl, cyclobutyl, cyclohexyl or cycloheptyl, and the like, which may be substituted by 1 to 3 substituents such as, for example, halogen atom, e.g., fluorine, chlorine, bromine, iodine, etc., hydroxy, alkoxy group of 1–6 carbon atoms, e.g., methoxy, ethoxy, propoxy, butoxy, hexyloxy, etc., mono- or di-($C_{1-6}$ alkoxy)phosphoryl group, e.g., methoxyphosphoryl, ethoxyphosphoryl, dimethoxyphosphoryl, di-ethoxyphosphoryl, etc., phosphono, and the like.

The substituted alkyl group is exemplified by trifluoromethyl, trifluoroethyl, trichloromethyl, hydroxymethyl, 2-hydroxyethyl, methoxyethyl, 1-methoxyethyl, 2-methoxyethyl, 2,2-diethoxyethyl, 2-diethoxyphosphorylethyl, phosphono, phosphonomethyl, and the like.

The substituted hydroxy in the "optionally substituted hydroxy group" is exemplified by alkoxy group, alkenyloxy group, aralkyloxy group, acyloxy group, aryloxy group, and the like. The "alkoxy group" includes, preferably, alkoxy group of 1–10 carbon atoms, e.g., methoxy, ethoxy, propoxy, butoxy, tert-butoxy, pentyloxy, hexyloxy, heptyloxy, nonyloxy, and the like, and cycloalkoxy group of 4–6 carbon atoms, e.g., cyclobutoxy, cyclopentoxy, cyclohexyloxy, and the like. The "alkenyloxy group" includes, preferably, those of 2–10 carbon atoms, e.g., allyloxy, crotyloxy, 2-pentenyloxy, 3-hexenyloxy, 2-cyclopentenylmethoxy, 2-cyclohexenylmethoxy, and the like. The "aralkyloxy group" includes, preferably, those of 6–19 carbon atoms, more preferably, $C_{6-14}$ aryl-$C_{1-4}$ alkyloxy, e.g., benzyloxy, phenethyloxy, and the like. The "acyloxy group" includes, preferably, alkanoyloxy group, for example, those of 2–10 carbon atoms, e.g., acetyloxy, propionyloxy, n-butyryloxy, hexanoyloxy, and the like. The "aryloxy group" includes, preferably, those of 6–14 carbon atoms, e.g., phenoxy, biphenyloxy, and the like. These groups may further be substituted by 1–3 substituents such as, for example, the above-mentioned halogen atom, hydroxy, alkoxy group of 1–6 carbon atoms, mono- or di-($C_{1-6}$ alkoxy)phosphoryl group, and the like. The substituted hydroxy group is exemplified by trifluoromethoxy, 2,2,2-trifluoroethoxy, difluoromethoxy, 2-methoxyethoxy, 4-chlorobenzyloxy, 2-(3,4-dimethoxy-phenyl)ethoxy, and the like.

The mercapto group in the "optionally substituted mercapto group" is exemplified by alkylthio group, aralkylthio group, acylthio group, and the like. The "alkylthio group" includes, preferably, alkylthio group of 1–10 carbon atoms, e.g., methylthio, ethylthio, propylthio, butylthio, pentylthio, hexylthio, heptylthio, nonylthio, and the like, and cycloalkylthio group of 4–6 carbon atoms, e.g., cyclobutylthio, cyclopentylthio, cyclohexylthio, and the like. The "aralkylthio group" includes, preferably, those of 7–19 carbon atoms, more preferably, $C_{6-14}$ aryl-$C_{1-4}$ alkylthio, e.g., benzylthio, phenethylthio, and the like. The "acylthio group" includes, preferably, alkanoylthio, for example, those of 2–10 carbon atoms, e.g., acetylthio, propionylthio, n-butyrylthio, hexanoylthio, and the like. These groups may further be substituted by 1–3 substituents such as, for example, the above-mentioned halogen atom, hydroxy, alkoxy group of 1–6 carbon atoms, mono- or di-($C_{1-6}$ alkoxy)phosphoryl group, and the like. The substituted thiol group is exemplified by trifluoromethylthio, 2,2,2-trifluoroethylthio, 2-methoxyethylthio, 4-chlorobenzylthio, 3,4-dichlorobenzylthio, 4-fluorobenzylthio, 2-(3,4-dimethoxyphenyl)ethylthio, and the like.

The substituent of the substituted amino group in the "optionally substituted amino group" includes the above-mentioned alkyl group of 1–10 carbon atoms, alkenyl group of 2–10 carbon atoms, e.g., allyl, vinyl, 2-penten-1-yl, 3-penten-1-yl, 2-hexen-1-yl, 3-hexen-1-yl, 2-cyclohexenyl, 2-cyclopentenyl, 2-methyl- 2-propen-1-yl, 3-methyl-2-buten-1-yl, and the like, aryl group of 6–14 carbon atoms, and aralkyl group of 7–19 carbon atoms, and these may be used alone or as two identical or different groups. These groups may be substituted by the above-mentioned halogen atom, alkoxy group of 1–6 carbon atoms, mono- or di-($C_{1-6}$ alkoxy)phosphoryl group, phosphono, and the like. The substituted amino group is exemplified by methylamino, dimethylamino, ethylamino, di-ethylamino, dibutylamino, diallylamino, cyclohexylamino, phenylamino or N-methyl-N-phenylamino, N-methyl-N-(4-chlorobenzyl)amino, N,N-di(2-methoxyethyl)amino, and the like.

As for the "acyl group", an organic carboxylic acyl group or sulfonic acyl group having a hydrocarbon group of 1–6 carbon atoms (e.g., methyl, ethyl, n-propyl, hexyl, phenyl, etc.) may be used. The "organic carboxylic acyl group" used includes, for example, formyl, alkyl-carbonyl group of 1–10 carbon atoms, e.g., acetyl, propionyl, butyryl, valeryl, pivaloyl, hexanoyl, octanoyl, cyclobutanecarbonyl, cyclohexanecarbonyl, cyclo-heptanecarbonyl, etc., alkenyl-carbonyl group of 2–10 carbon atoms, e.g., crotonyl, 2-cyclohexenecarbonyl, etc., aryl-carbonyl group of 6–14 carbon atoms, e.g., benzoyl, etc., aralkyl-carbonyl group of 7–19 carbon atoms, e.g., benzylcarbonyl, benzhydrylcarbonyl, etc., 5- or 6-membered aromatic heterocyclic carbonyl group, e.g., nicotinoyl, 4-thiazolyl-carbonyl, etc., 5- or 6-membered aromatic heterocyclic acetyl group, e.g., 3-pyridylacetyl, 4-thiazolylacetyl, etc. The "sulfonic acyl group having a hydrocarbon group of 1–6 carbon atoms" used includes, for example, methanesulfonyl, ethanesulfonyl, and the like. These groups may be substitued by 1–3 substituents, for example, the above-mentioned halogen atom, hydroxy, alkoxy group of 1–6 carbon atoms, amino, and the like. The acyl group is exemplified by trifluoroacetyl, trichloroacetyl, 4-methoxybutyryl, 3-cyclohexyloxypropionyl, 4-chlorobenzoyl, 3,4-dimethoxybenzoyl, and the like.

The "mono- or di-alkoxyphosphoryl group" used includes, for example, mono-$C_{1-6}$ alkoxyphosphoryl group such as methoxyphosphoryl, ethoxyphosphoryl, propoxyphosphoryl, isopropoxyphosphoryl, butoxyphosphoryl, pentyloxyphosphoryl, hexyloxyphosphoryl, and the like, and di-$C_{1-6}$ alkoxyphosphoryl group such as dimethoxyphosphoryl, diethoxyphosphoryl, di-propoxyphosphoryl, diisopropoxyphosphoryl, dibutoxy-phosphoryl, dipentyloxyphosphoryl, dihexyloxyphosphoryl, and the like. Preferably, di-$C_{1-6}$ alkoxyphosphoryl group, for example, dimethoxyphosphoryl, diethoxyphosphoryl, di-propoxyphosphoryl, diisopropoxyphosphoryl, ethylenedioxy-phosphoryl, dibutoxyphosphoryl, and the like may be used.

The aryl group in the "optionally substituted aryl group" used includes, preferably, those of 6–14 carbon atoms, for example, phenyl, naphthyl, anthryl and the like. These groups may be substituted by 1–3 substituents such as alkyl group of 1–10 carbon atoms, halogen atom, hydroxy, alkoxy group of 1–6 carbon atoms, and the like. The substituted aryl group is exemplified by 4-chlorophenyl, 3,4-dimethoxyphenyl, 4-cyclohexylphenyl, 5,6,7,8-tetrahydro-2-naphthyl, and the like.

The aralkyl group in the "optionally substituted aralkyl group" used includes, preferably, those of 7–19 carbon atoms, for example, benzyl, naphthylethyl, trityl, and the like, and these groups may be substituted on the aromatic ring by 1–3 substituents such as alkyl group of 1–10 carbon atoms, halogen atom, hydroxy, alkoxy group of 1–6 carbon atoms, and the like. The substituted aralkyl group is exemplified by 4-chlorobenzyl, 3,4-dimethoxybenzyl, 4-cyclohexylbenzyl, 5,6,7,8-tetrahydro-2-naphthylethyl, and the like.

The aromatic heterocyclic group in the "optionally substituted aromatic heterocyclic group" used includes, preferably, 5- or 6-membered ones having 1 to 4 of nitrogen atom, oxygen atom and/or sulfur atom, for example, furyl, thienyl, imidazolyl, thiazolyl, oxazolyl, thidiazolyl, and the like. These groups may be substituted by 1–3 substituents such as alkyl group of 1–10 carbon atoms, halogen atom, hydroxy, alkoxy group of 1–6 carbon atoms, and the like.

When two alkyl groups are placed adjacent to each other on the benzene ring A, they may be bound to each other to form an alkylene group of the formula: $(CH_2)_L$— [wherein L is an integer of 3–5] (e.g., trimethylene, tetramethylene, pentamethylene, etc.), and when two alkoxy groups are placed adjacent to each other, they may form an alkylenedioxy group of the formula: $-O-(CH_2)_m-O-$ [wherein m is an integer of 1–4] (e.g., methylenedioxy, ethylenedioxy, trimethylenedioxy, etc.). In such a case, a 5- to 8-membered ring is formed together with the carbon atoms on the benzene ring.

The preferred substituent on the ring A includes, for example, halogen atom, $C_{1-10}$ alkyl group, $C_{1-10}$ alkoxy group, alkylenedioxy group of the formula: $-O-(CH_2)_m-O-$ [wherein m is an integer of 1–4], $C_{1-10}$ alkylthio group, and the like, wherein the number of the substituent is preferably 1 or 2.

In the above-mentioned formulae, the non-aromatic heterocycle in the optionally substituted non-aromatic heterocyclic group represented by $R^1$ includes 3- to 8-membered ones containing 1 to 4 heteroatoms selected from the group consisting of nitrogen atom, sulfur atom and oxygen atom. Such a heterocycle is exemplified by oxirane, azetidine, oxetane, thietane, pyrrolidine, tetrahydrofuran, thiolane, piperidine, tetrahydropyran, morpholine, thiomorpholine, piperazine, homopiperidine, pyrroline, imidazolidine, thiazoline, iso-thiazoline, thiazolidine, isothiazolidine, imidazoline, oxazoline, oxazolidine, oxadiazolidine, oxathiazolidine, dithiazolidine, thiadiazolidine, and the like. In particular, the 4- to 7-membered non-aromatic heterocycle is preferred, and especially, 5- or 6-membered one is preferred.

In the above-mentioned formulae, the substituent on the optionally substituted non-aromatic heterocyclic group includes, for example, (i) halogen atom (e.g., fluorine, chlorine, bromine, iodine, etc.), (ii) hydroxy or oxo, (iii) alkoxy group of 1–6 carbon atoms (e.g., methoxy, ethoxy, propoxy, butoxy, tert-butoxy, pentyloxy, hexyloxy, etc.), (iv) amino group optionally substituted by alkyl group of 1–6 carbon atoms (e.g., methyl, ethyl, propyl, isopropyl, butyl, isobutyl, sec-butyl, tert-butyl, pentyl, isopentyl, neopentyl, hexyl, etc.) (e.g., amino, methylamino, ethylamino, dimethylamino, diethylamino, dipropylamino, etc.), (v) amino group substituted by an acyl group (e.g., alkanoyl group of 1–10 carbon atoms, etc.) (e.g., acetylamino, propionylamino, benzoylamino, etc.), (vi) carbamoyl group optionally substituted by an alkyl group or groups of 1–6 carbon atoms (e.g., carbamoyl, methylcarbamoyl, dimethylcarbamoyl, diethylcarbamoyl, etc.), (vii) alkoxycarbonyl group of 1–6 carbon atoms (e.g., methoxycarbonyl, ethoxycarbonyl, propoxycarbonyl, etc.), and the like. The number of substituents is preferably 1 to 4.

The substituent includes, preferably, halogen atom, hydroxy or oxo, $C_{1-10}$ alkyl, $C_{1-6}$ alkoxy, $C_{1-6}$ acyl, amino, mono- or di-$C_{1-6}$ alkylamino, mono- or di-$C_{1-6}$ alkylsulfonyl, carboxy or $C_{1-6}$ alkoxy-carbonyl, and the like, and the number of the substituent is preferably 1 to 3.

The optionally substituted non-aromatic heterocyclic group is exmplified by oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, homopiperidyl, 4-oxopiperidyl, pyrrolinyl, imidazolidinyl, 4-formylpiperadinyl, 4-methanesulfonylpiperadinyl, 3-hydroxypyrrolidinyl, 2,4-dioxothiazolidin-5-yl, 2,4-dioxothiazolidin-3-yl, hydantoin-3-yl, 2,6-dioxopiperidinyl, 1-methylhydantoin-3-yl, succinimido, 2-oxazolidon-3-yl, 2,4-dioxooxazolidin-5-yl, 2,4-dioxooxazolidin-3-yl, 1,1-dioxotetrahydro-2H-1-isothiazol-2-yl, 3,5-dioxo-1,2,4-oxadiazolidin-2-yl, and the like. These non-aromatic heterocyclic groups may be condensed with a benzene ring, a 6-membered ring containing 2 or less nitrogen atoms, or a 5-membered ring containing one sulfur atom. The condensed non-aromatic heterocyclic group is exemplified by chromanyl, isochromanyl, indolinyl, isoindolinyl, thiochromanyl, isothiochromanyl, and the like.

In the above-mentioned formulae, the preferred non-aromatic heterocycle of the optionally substituted non-aromatic heterocyclic group includes 5- or 6-membered non-aromatic heterocycles containing at least one nitrogen atom, 5- or 6-membered non-aromatic heterocycles containing one nitrogen atom and one sulfur atom or oxygen atom, and the like.

The preferred 5- or 6-membered non-aromatic heterocycles containing at least one nitrogen atom include, for example, pyrrolidine, imidazolidine, thiazolidine, isothiazolidine, oxazolidine, oxadiazolidine, piperidine, piperazine, thio-morpholine, morpholine, and the like.

The preferred 5- or 6-membered non-aromatic heterocycles containing one nitrogen atom and one sulfur atom or oxygen atom include, for example, thiazolidine, oxazolidine, thio-morpholine, morpholine, and the like.

As the hydrocarbon group in "the optionally substituted hydrocarbon group" represented by $R^2$, $R^3$ or $R^{31}$ in the above-mentioned formulae or by $R^{21}$ as mentioned below, the same group as mentioned above, that is, alkyl group (preferably, alkyl of 1–10 carbon atoms), alkenyl group (preferably, alkenyl of 2–10 carbon atoms), aryl group (preferably, aryl of 6–14 carbon atoms), aralkyl group (preferably, aralkyl of 7–19 carbon atoms), and the like may be used. As the substituent on the hydrocarbon group, the above-mentioned halogen atom, di-$C_{1-6}$ alkoxyphosphoryl group, phosphono, and the like may be used.

As the hydrocarbon group in "the optionally substituted hydrocarbon group", for example, a straight or branched $C_{1-6}$ alkyl group such as methyl, ethyl, propyl, isopropyl, butyl, iso-butyl, sec-butyl, tert-butyl, pentyl, isopentyl, neopentyl, hexyl, and the like, is preferred. Particularly, a $C_{1-4}$ alkyl group is preferred.

As the above-mentioned groups $R^2$, $R^3$, $R^{21}$ and $R^{31}$, an unsubstituted hydrocarbon group is particularly preferred.

The $C_{1-10}$ alkyl group represented by $R^4$ and $R^5$ in the above-mentioned formulae includes, for example, straight or branched alkyl groups such as methyl, ethyl, propyl, isopropyl, butyl, isobutyl, sec-butyl, tert-butyl, pentyl, isopentyl, neopentyl, hexyl, and the like. In particular, a $C_{1-6}$ alkyl group, especially, a $C_{1-4}$ alkyl group, is preferred.

The $C_{1-4}$ alkylene chain formed by taking $R^4$ and $R^5$ together in the above-mentioned formulae, includes, for example, methylene, ethylene, trimethylene, tetramethylene, and the like. In the above-mentioned formulae, n is an integer of 0–3, preferably, 1 or 2.

In the above-mentioned formulae, $R^{11}$ indicates dioxopyrrolidinyl, mono- or di-oxopiperidinyl, thiomorpholinyl, thiazolidinyl, dioxothiazolidinyl, 1-methyldioxoimidazolinyl, dioxooxazolidinyl, dioxotetrahydroisothiazolinyl, dioxooxadiazolidinyl, and the like, and in particular, 2,5-dioxopyrrolidinyl, 4-oxopiperidinyl, 2,6-dioxopiperidinyl, thiomorpholinyl, thiazolidinyl, 2,4-dioxothiazolidinyl, 1-methyl-2,4-dioxoimidazolinyl, 2,4-dioxooxazolidinyl, 1,1-dioxotetrahydro-2H-isothiazolinyl, and 2,4-dioxooxadiazolidinyl are preferred.

The compounds of the invention represented by the formula (I)(hereinafter referred to as Compound (I)) include preferably optically active compounds of (2R, 4S)-configuration represented by the formula:

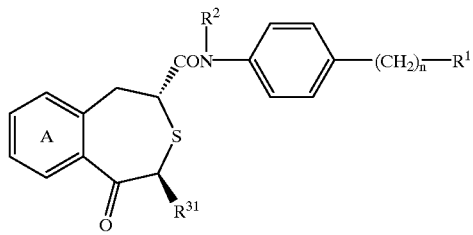

wherein each symbol has the same meanings as mentioned above. Moreover, it is preferred that the compounds substantially contain no compounds of (2S,4R)-configuration and their optical purity is approximately 100%.

Compounds (I) of the invention can be prepared by reacting compounds of the formula (II) (including their optically active isomers), reactive derivatives thereof at the carboxyl group or salts thereof, with compounds of the formula (III), reactive derivatives thereof at the amino group or salts thereof, as shown in the following reaction scheme.

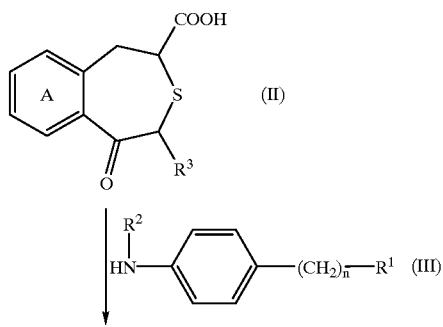

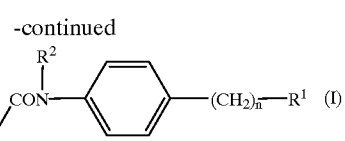

The preferred reactive derivatives at the carboxyl group of compounds of the formula (II)(including their optically active isomers) include, for example, acid halides (e.g., acid chlorides, etc.); acid azides; acid anhydrides [for example, mixed acid anhydrides with acids, e.g., substituted phosphoric acids such as dialkylphosphoric acids, phenylphosphoric acid, diphenylphosphoric acid, dibenzylphosphoric acid, halogeno-phosphoric acids, etc., dialkylphosphorous acids, sulfurous acid, thiosulfuric acid, sulfuric acid, sulfonic acids such as methanesulfonic acid, etc., aliphatic carboxylic acids such as acetic acid, propionic acid, butyric acid, isobutyric acid, pivalic acid, pentanoic acid, isopentanoic acid, trichloroacetic acid, etc., or aromatic carboxylic acids such as benzoic acid, etc.; symmetric acid anhydrides], active amides [e.g., activated amides with imidazole, 4-substituted imidazoles, dimethylpyrazole, triazole, or tetrazole], active esters [e.g., activated esters such as cyanomethyl esters, methoxymethyl esters, dimethyliminomethyl esters, vinyl esters, propargyl esters, p-nitrophenyl esters, trichlorophenyl esters, pentachlorophenyl esters, mesylphenyl esters, phenylazophenyl esters, phenyl thioesters, p-nitrophenyl esters, p-cresyl thioesters, carboxymethyl thioesters, pyranyl esters, pyridyl esters, piperidinyl esters, 8-quinolyl thioesters, etc.]; esters [e.g., esters with N-hydroxy compounds such as N,N-dimethylhydroxyamine, 1-hydroxy-2-(1H)-pyridone, N-hydroxysuccinimide, N-hydroxyphthalimide, 1-hydroxy-1H-benzotriazole, etc.]. These reactive derivatives may optionally be selected in accordance with the species of the compounds of the formula (II) to be used.

The preferred salts of the reactive derivatives of the compounds represented by the formula (II) include, for example, alkali metal salts, e.g., sodium salts, potassium salts, etc., alkaline earth metal salts, e.g., calcium salts, magnesium salts, etc., ammonium salts, for example, such base salts as organic base salts, e.g., trimethylamine salts, triethylamine salts, pyridine salts, picoline salts, dicyclohexylamine salts, N,N-dibenzylethylenediamine salts, etc.

The preferred reactive derivatives at the amino group in the compounds of the formula (III) include, for example, Schiff base-type imino derivatives or their enamine-type tautomers produced by reaction of the compounds of the formula (III) with carbonyl compounds such as aldehydes, ketones, etc.; silyl derivatives produced by reaction of the compounds of the formula (III) with silyl compounds such as bis(trimethylsilyl)acetamide, mono(trimethylsilyl)acetamide, bis(trimethylsilyl)urea, etc.; derivatives produced by reaction of the compounds of the formula (III) with phosphorus trichloride or phosgene; and the like.

The reaction of the invention as shown in the above-illustrated Reaction Scheme 1 may be carried out in an organic solvent giving no adverse effect to the reaction, for example, alcohol (e.g., methanol, ethanol, n-propanol, isopropanol, n-butanol, 3-pentanol, etc.), aromatic hydrocarbon (e.g., benzene, toluene, xylene, etc.), halogenohydrocarbon (e.g., carbon tetrachloride, 1,2-dichloroethane, dichloromethane, chloroform, monochloromethane, ethylene chloride, etc.), saturated hydrocarbon (e.g., hexane, heptane, cyclohexane, etc.), ether (e.g., diethyl ether, tetrahydrofuran, dioxane, dimethoxyethane, isopropyl ether, etc.), ketone (e.g., acetone, methyl ethyl ketone, etc.), nitrile (e.g., acetonitrile, propionitrile, etc.), sulfoxide (e.g., dimethylsulfoxide, etc.), amide (N,N-dimethylformamide, N,N-dimethylacetamide, etc.), ester (e.g., methyl acetate, ethyl acetate, etc.), carboxylic acid (e.g., acetic acid, propionic acid), tertiary amine (e.g., pyridine, etc.), or the like, or in an aqueous mixture with any of these conventional solvents.

Particularly, the reaction is preferably carried out in water or a conventional solvent, for example, an alcohol (e.g., methanol, ethanol, etc.), acetone, dioxane, acetonitrile, chloroform, dichloromethane, ethylene chloride, tetrahydrofuran, ethyl acetate, N,N-dimethylformamide, pyridine, or the like.

In the above reaction, when the compounds of the formula (II) are used in a form of free acids or salts thereof, it is appropriate to carry out the reaction so as to be accelerated in the presence of a conventional condensing agent, for example, N,N'-dicyclohexylcarbodiimide; N-cyclohexyl-N'-morpholino-ethylcarbodiimide; N-cyclohexyl-N'-(4-diethylaminocyclo-hexyl)carbodiimide; N,N'-diethylcarbodiimide, N,N'-diiso-propylcarbodiimide, N-ethyl-N'-(3-dimethylaminopropyl)-carbodiimide; N,N'-carbonylbis-(2-methylimidazole); penta-methyleneketene-N-cyclohexylimine; diphenylketene-N-cyclo-hexylimine; ethoxyacetylene; 1-alkoxy-1-chloroethylene; trialkyl phosphate; ethyl polyphosphate; isopropyl poly-phosphate; phosphorus oxychloride; diphenylphosphorylazide; thionyl chloride; oxalyl chloride; lower alkyl haloformate, e.g., ethyl chloroformate, isopropyl chloroformate, etc.; triphenylphosphine; 2-ethyl-7-hydroxybenzisoxazolium salt, 2-ethyl-5-(m-sulfophenyl)isoxazolium hydroxide inner salt; N-hydroxybenzotriazole; 1-(p-chlorobenzenesulfonyloxy)-6-chloro-1H-benzotriazole; so-called Vilsmeier's reagent prepared from N,N'-dimethylformamide on reaction with thionyl chloride, phosgene, trichloromethyl chloroformate, phosphorus oxychloride, etc.; and the like.

The reaction may also be carried out in the presence of an inorganic base or organic base, for example, alkali metal hydrogencarbonate (e.g., sodium hydrogencarbonate), tri($C_{1-4}$)alkylamine (e.g., trimethylamine), pyridine, N-($C_{1-4}$)-alkylmorpholine (e.g., N-methylmorpholine), N,N-di($C_{1-4}$)-alkylbenzylamine (N,N-dimethylbenzylamine), and the like.

The reaction temperature is not limited specifically, and the reaction may be carried out usually under cooling or warming (about −10 to 120° C., preferably, about −5 to 50° C.). The reaction time is usually abut 0.5 to about 100 hours, preferably, about 1 to about 50 hours.

When the compounds of the formula (III) have any other active substituent disturbing the reaction, such a substituent may preferably be protected prior to the reaction according to a conventional way and then deprotected after the reaction completion.

Thus resulting compounds (I) or salts thereof can be isolated and purified by means of a well-known procedure for separation and purification, such as condensation, evaporation under reduced pressure, extraction with a solvent, crystallization, recrystallization, dissolution to another solvent, chromatography, and the like.

The compounds of the formula (II) or reactive derivatives thereof at the carboxy group (used as the starting compounds in the method of the invention) can be prepared according to a per se known method, for example, the method as disclosed in JP-A 08-231569/1996 or its analogous methods.

In the compounds of the formula (III), the compounds wherein n is 1 and the non-aromatic heterocyclic group represented by $R^1$ has a bond attached to the nitrogen atom, can be prepared according to the method as illustrated in the following Reaction Scheme or its equivalent method, or alternatively according to the method as described in Reference Examples as mentioned below or its equivalent method.

[77]

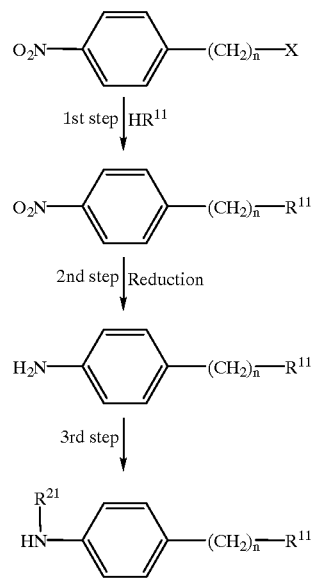

More specifically, the reaction of the 1st step is carried out by reacting 4-nitrophenylalkyl halides with optionally substituted non-aromatic heterocycles (represented by $HR^{11}$; $R^{11}$ represents a non-aromatic heterocyclic group having a bond attached to the nitrogen atom) in the presence of a base in an appropriate solvent. As the 4-nitrophenylalkyl halides, 4-nitrobenzyl chloride is exemplified.

The preferred base includes, for example, inorganic bases such as sodium hydride, potassium carbonate, etc., and organic bases such as triethylamine, pyridine, 1,8-diazabicyclo[5.4.0]undecen-7-ene (DBU), etc.

The solvent includes, for example, ketones (e.g., acetone, methyl ethyl ketone, etc.), nitriles (e.g., acetonitrile), ethers (e.g., tetrahydrofuran), esters (e.g., ethyl acetate), amides (e.g., N,N-dimethylformamide), and the like. The reaction temperature is about 0 to 60° C. The reaction time is about 0.5 to 50 hours.

In the 2nd step, reduction is conducted. The reducing agent or method used in the reduction includes, for example, a combination of a metal (e.g., iron, zinc, zinc amalgam, etc.) or a salt of chromium compound (e.g., chromous chloride, chromous acetate, etc.) with an organic or inorganic acid (e.g., acetic acid, propionic acid, hydrochloric acid, etc.); catalytic hydrogenation in the presence of a metal catalyst (e.g., palladium-carbon, Raney nickel, etc.); and the like.

The solvent used in the reaction includes, for example, alcohols (e.g., methanol, ethanol), ethers (e.g., tetrahydrofuran), esters (e.g., ethyl acetate), carboxylic acids (e.g., acetic acid), and the like. The reaction temperature is about 0 to 60° C. The reaction time is approximately 0.5 to 50 hours.

In the 3rd step, the group $R^{21}$ ($R^{21}$ is an optionally substituted hydrocarbon group) is introduced into the amino group. The reaction may be carried out in the same manner as described in Bulletin de la Societe Chimique de France Partie 2, 1970, Issue 5, 1901–1907, or its equivalent method.

The compounds (III)[including the compounds (III')] can be used as the starting compounds in producing Compounds (I) of the invention.

As the salts of the starting compounds (II), (III) and the objective compounds (I) of the invention, pharmaceutically acceptable salts are preferred, including, for example, salts with inorganic bases, salts with organic bases, salts with inorganic acids, salts with organic acids, salts with basic or acidic amino acids, and the like. The preferred salts with inorganic bases are exemplified by alkali metal salts, e.g., sodium salts, potassium salts, etc.; alkaline earth metal salts, e.g., calcium salts, magnesium salts, etc.; as well as aluminum salts, ammonium salts, and the like. The preferred salts with organic bases are exemplified by salts of trimethylamine, triethylamine, pyridine, picoline, ethanolamine, diethanolamine, triethanolamine, dicyclohexylamine, N,N'-dibenzylethylenediamine, and the like. The preferred salts with inorganic acids are exemplified by those of hydrochloric acid, hydrobromic acid, nitric acid, sulfuric acid, phosphoric acid, and the like. The preferred salts with organic acids are exemplified by those of formic acid, acetic acid, trifluoroacetic acid, fumaric acid, oxalic acid, tartaric acid, maleic acid, citric acid, succinic acid, malic acid, methanesulfonic acid, benzensulfonic acid, p-toluenesulfonic acid, and the like. The preferred salts with basic amino acids are exemplified by those of arginine, lysine, ornithine, and the like, and the salts with acidic amino acids are those of aspartic acid, glutaric acid, and the like.

The prodrugs of Compounds (I) of the invention are compounds convertible into Compounds (I) on action of enzymes or gastric acid under physiological conditions in a living body, that is, compounds which are enzymatically oxidized, reduced or hydrolyzed to give Compounds (I), or compounds which are hydrolyzed with gastric acid or the like to give Compounds (I). The prodrugs of Compounds (I) of the invention include: when Compounds (I) have an amino group as substituent, then acylated, alkylated or phosphorylated compounds at the amino group; when Compounds (I) have a hydroxy group as substituent, then acylated, alkylated, phosphorylated or borated compounds at the hydroxy group; and when Compounds (I) have a carboxyl group as substituent, then esterified or amide-formed compounds. These compounds may be prepared from Compounds (I) in a per se known method.

Alternatively, the prodrug of Compounds (I) may be those which can be converted into Compounds (I) in a physiological condition as described in "Development of Drugs", vol. 7, Molecular Design, pp. 163–198 (1990), Hirokawa Publishing Company.

Compounds (I) of the invention and salts thereof have a potent osteogenesis promoting effect, chondrogenesis promoting effect, cartilage destruction suppressing effect, and cartilage cell differentiation induction promoting effect, and in addition they are superior in clinically useful characteristics such as stability, absorption (particularly, oral absorption), bioavailability, and the like. In addition, their toxicity is low. Compounds (I) of the invention and salts thereof, accordingly, can be used in prevention and treatment of a variety of bone diseases, for example, osteoporosis, fracture, cartilage defect, chronic rheumatoid arthritis involving cartilage, and osteoarthritis of a knee involving cartilage in mammals (e.g., human, rat, mouse, dog, rabbit, cat, cattle, swine, etc.).

Compounds (I) of the invention and salts thereof, since they exhibit a potent alkaline phosphatase-inducing activity, have an excellent osteogenesis promoting effect and chondrogenesis promoting effect, and are useful as prophylactic or therapeutic agents for metabolic bone diseases and metabolic cartilage diseases including osteoporosis. Moreover, the osteogenesis promoting agents and chondrogenesis promoting agents which contain Compounds (I) of the invention or salts thereof having such effects, can be used as prophylactic or therapeutic agents for bone diseases and cartilage diseases such as fracture, refracture, bone defect, osteomalacia, Paget's syndrome in bone, rigid myelitis, chronic rheumatoid arthritis, osteoarthritis (e.g., osteoarthritis of the knee), osteoarthritis involving cartilage, and the like in the orthopaedic region, as well as used as osseous tissue restoration agents after surgery for multiple myeloma, lung cancer, breast cancer, and the like. Moreover, in the dental field, they are expected to apply to treatment of periodontal diseases, restoration of periodontal tissue defects in periodontal diseases, stabilization of artificial tooth roots, residual ridge formation and repair of cleft palate.

Compounds (I) of the invention and salts thereof, when used as prophylactic or therapeutic agents for osteoporosis, fracture, cartilage defect, etc., may be administered orally at a daily dose of about 5 mg to about 1000 mg, preferably about 10 mg to about 500 mg, as active ingredient [Compound (I) or salt thereof of the invention] for an adult (body weight 50 kg) in 1 to 3 divided doses while the dose varies depending on the state or weight of a patient, the administration manner and the like.

In parenteral administration, they may be administered at a daily dose of about 1 mg to about 3000 mg, preferably about 10 mg to 300 mg, as active ingredient [Compound (I) or salt thereof of the invention] for an adult (body weight 50 kg) in 1 to 3 divided doses.

Compound (I) or salt thereof of the invention can be used in combination with other bone resorption promoting agents or osteogenesis promoting agents. The agents used in combination are exemplified by vitamins $D_3$ (e.g., 1α-hydroxyvitamin $D_3$, 1α-2,5-dihydroxyvitamin $D_3$, flocalcitriol, secalciferol, etc.), calcitonins (e.g., eel calcitonin, salmon calcitonin, porcine calcitonin, avicatonin, etc.), bisphosphonic acids (e.g., etidronate, simadronate, alendronate, tiludronate, risedronate, clodronate, etc.), sex hormone related compounds (e.g., tibolone, estradiol, osaterone, raloxifene, droloxifene, ormeloxifene, tamoxifene, mifepristone, etc.), ipriflavone, vitamins $K_2$ (e.g., menatetrenone), sodium fluoride, parathyroid hormones (PTH)(e.g., PTH (1–34), PTH (1–84), PTH (1–36), etc.), and the like.

Compounds (I) or salts thereof of the invention may be combined with pharmaceutically acceptable carriers to form solid preparations such as tablets, capsules, granules, powder, and the like; or liquid preparations such as syrup, injection, and the like, and administered orally or parenterally. They may also be formed into percutaneously administrable preparations such as patch, poultice, ointment (including cream), plaster, tape, lotion, liquid preparation, suspension, emulsion, aerosol, and the like.

As the pharmaceutically acceptable carriers, a variety of conventional organic or inorganic carrier materials usually added to pharmaceutical preparations can be used, including excipients, lubricants, binders, disintegrators, etc., in solid preparations; solvents, dissolution aids, suspending agents, isotonization agents, buffering agents, soothing agents, etc., in liquid preparations. If required, pharmaceutical additives such as preservatives, antioxidants, stabilizers, coloring agents, sweeteners, and the like may be added. The preferred excipients include, for example, lactose, refined sugar, D-mannitol, starch, crystalline cellulose, light silicic anhydride, and the like. The preferred lubricants include, for example, magnesium stearate, calcium stearate, talc, colloidal silica, and the like. The preferred binders include, for example, crystalline cellulose, α-starch, refined sugar, D-mannitol, dextrin, hydroxypropyl cellulose, hydroxypropyl methyl cellulose, polyvinylpyrrolidone, and the like. The preferred disintegrators include, for example, starch, carboxymethyl cellulose, carboxymethyl cellulose calcium, croscarmellose sodium, carboxymethyl starch sodium, low-substituted hydroxypropyl cellulose, and the like. The preferred solvents include, for example, water for injection, alcohol, propylene glycol, macrogol, sesame oil, corn oil, and the like.

If required, the oral preparation may be coated in a per se conventional manner in order to mask its taste or give enteric coating preparations or sustained-release preparations. The coating agents include, for example, hydroxypropyl methyl cellulose, ethyl cellulose, hydroxymethyl cellulose, hydroxypropyl cellulose, polyoxyethylene glycol, Tween 80, Pluronic F68, cellulose acetate phthalate, hydroxypropyl methyl cellulose phthalate, hydroxymethyl cellulose acetate succinate, Eudragit (methacrylic acid/acrylic acid copolymer; Rohm Pharma GmbH, Germany), and the like.

The preferred dissolution aids include, for example, polyethylene glycol, propylene glycol, D-mannitol, benzyl benzoate, ethanol, trisaminomethane, cholesterol, triethanolamine, sodium carbonate, sodium citrate, and the like. The preferred suspending agents include, for example, surface activators such as stearyl triethanolamine, sodium lauryl sulfate, laurylaminopropionic acid, lecithin, benzalkonium chloride, benzethonium chloride, glycerin monostearate, etc.; and hydrophilic high molecular weight materials such as polyvinyl alcohol, polyvinylpyrrolidone, carboxymethylcellulose sodium, methylcellulose, hydroxymethyl cellulose, hydroxyethyl cellulose, hydroxypropyl cellulose, etc. The preferred isotonization agents include, for example, sodium chloride, glycerin, D-mannitol, and the like. The preferred buffering agents include, for example, buffer solutions containing phosphate, acetate, carbonate, citrate, and the like. The preferred soothing agents include, for example, benzyl alcohol, etc. The preferred preservatives include, for example, peroxybenzoic acid esters, chlorobutanol, benzyl alcohol, phenethyl alcohol, dehydroacetic acid, sorbic acid, and the like. The preferred anti-oxidants include, for example, sulfites, ascorbic acid, and the like.

In addition to the formulations prepared according to the above-mentioned conventional pharmaceutical technique, Compounds (I) or salts thereof of the invention may also be formulated into sustained-release preparations according to a technique for sustained-release formulation. A method for preparing sustained-release preparations, as described in JP-A 9-263545/1997, comprises dispersing Compound (I) into an aliphatic polyester such as lactic acid-glycolic acid copolymer according to the in-water drying method, phase separation method, spray drying method, and the like. The sustained-release preparations prepared by these methods can be applied locally as a suspension of microcapsules or microspheres.

Compounds (I) or salts thereof of the invention are preferably added to a pharmaceutical composition together with polyethylene glycol, as described in JP-A 10-338646/1998.

Moreover, when administered directly into the cavitas articularis as a local medicament, Compound (I) or salt thereof may be dispersed into a hyaluronic acid preparation for injection (for example, Kaken Pharm. Co., Ltd.; ALTZ injection) as a dispersing agent. Hyaluronic acid used in a dispersing medium may be used in a form of non-toxic salts, for example, alkali metal salts, e.g., salts with sodium, potassium, etc., or alkaline earth metal salts, e.g., salts with magnesium, calcium, etc., and particularly, the sodium salt is preferably used. The average molecular weight of hyaluronic acid or its non-toxic salts to be used is approximately 200,000–5,000,000, preferably, approximately 500,000–3,000,000, more preferably, approximately 700,000–2,500,000 (viscometrically).

The final concentration of hyaluronic acid or its sodium salt in the dispersing medium is preferably fixed at less than 1% (w/v) giving appropriate viscosity in view of ease of various operations or administration, particularly less than 0.02–1%, more preferably about 0.1–1% (w/v).

Into the above-mentioned dispersing medium, it is possible to add a pH regulator, local anesthetic, antibiotic, dissolution aid, isotonization agent, adsorption preventing agent, glycosaminoglycan, polysaccharide, and the like in a per se known manner. The preferred additives are, for example, mannitol, sorbitol, sodium chloride, glycine, ammonium acetate, or substantially pharmaceutically inactive water-soluble proteins injectable to the body. The glycosaminoglycan includes, for example, hyaluronic acid, chondroitin, chondroitin sulfate A, chondroitin sulfate C, dermatan sulfate, heparin, heparan sulfate, keratin sulfate, and the like. The polysaccharide includes acidic ones such as alginic acid.

The above-mentioned water-soluble proteins include those that are soluble in water, physiological saline, or buffer solution, for example, human serum albumin, human serum globulin, collagen, gelatin, and the like. When a water-soluble protein is contained in a dispersing medium, the content of the protein is preferably in 0.05–50 mg per dosage, more preferably 0.5–20 mg, particularly 0.75–10 mg.

The above-mentioned pH regulator includes, for example, glycine, ammonium acetate, citric acid, hydrochloric acid, sodium hydroxide, and the like. The above-mentioned local anesthetic includes, for example, chlorobutanol, lidocaine hydrochloride, and the like. The above-mentioned antibiotics include, for example, gentamicin, etc. The above-mentioned dissolution aids include, for example, glycerin, polyethylene glycol 400, and the like. The above-mentioned isotonization agents include, for example, mannitol, sorbitol, sodium chloride, and the like. The above-mentioned adsorption preventing agents include, for example, polyoxyethylene sorbitan mono-oleate, etc.

The pharmaceutical preparation may also contain phosphoric acid or its salts (for example, sodium phosphate, potassium phosphate, etc.). When the preparation for injection contains phosphoric acid or its salts, the concentration of sodium phosphate or potassium phosphate is in about 0.1 mM to 500 mM, preferably about 1 mM to 100 mM.

BEST MODE FOR CARRYING OUT THE INVENTION

EXAMPLES

The invention will be explained more in detail based on the following Reference Examples, Examples, and Test Example, but the invention is not restricted by these examples.

Reference Example 1

Preparation of 3-(4-Aminobenzyl)-2,4-dioxothiazolidine

To a solution of 4-nitrobenzyl bromide (8.00 g) and potassium carbonate (7.68 g) in N,N-dimethylformamide (DMF)(80 ml) was added 2,4-thiazolidinedione (6.51 g), and the mixture was stirred at room temperature for 14 hours. Insoluble material was filtered off, and the mother liquor was evaporated under reduced pressure. The residue was dissolved in ethyl acetate, and washed with diluted hydrochloric acid, water and saturated brine, successively. The solution was dried (MgSO$_4$) and evaporated under reduced pressure, and the precipitated crystals were collected by filtration under suction to give 3-(4-nitrobenzyl)-2,4-dioxothiazolidine (8.45 g, 34%).

In a mixture of ethanol (400 ml) and ethyl acetate (400 ml) was dissolved 3-(4-nitrobenzyl)-2,4-dioxothiazolidine (8.25 g), to which was added 5% palladium-carbon (2.00 g), and the mixture was stirred in hydrogen atmosphere at room temperature for 8 hours. Insoluble material was filtered off, the mother liquor was evaporated under reduced pressure, and the precipitated crystals were collected by filtration. Re-crystallization from isopropyl ether afforded the title compound (6.29 g, 87%).

$^1$H-NMR (CDCl$_3$) δ: 3.60–3.80 (2H, m), 3.90 (2H, s), 4.65 (2H, s), 6.61 (2H, d, J=8.4 Hz), 7.22 (2H, d, J=8.4 Hz).

Reference Examples 2–8

According to the same manner as in Reference Example 1, the compounds shown in the following Table 1 were obtained.

TABLE 1

H$_2$N—⟨phenyl⟩—CH$_2$—R$^1$

| Ref. Ex. No. | R$^1$ | yield 1st step/ 2nd step | $^1$NMR (δppm in CDCl$_3$)* |
|---|---|---|---|
| 2 | (glutarimide) | 78/94 | 1.91(2H,quintet, J=6.4Hz), 2.64(2H, t, J=6.4Hz), 3.55–3.80(2H, br), 4.83 (2H, s), 6.59(2H, dlike, J=8.5Hz), 7.22(2H, dlike, J=8.5Hz). |
| 3 | (N-methyl hydantoin) | 70 (total yield) | 2.97(3H, s), 3.82(2H, s), 4.53(2H, s), 6.62(2H, dt, J=8.2, 1.0 Hz), 7.24(2H, dt, J=8.2, 1.0 Hz). |
| 4 | (2,4-dioxooxazolidine) | 20 (total yield) | 4.39(2H, s), 4.86(2H, s), 6.51(2H, d, J=8.0Hz), 6.98(2H, d, J=8.0Hz) |
| 5 | (succinimide) | 93/93 | 2.67(4H, s), 3.67(2H,s), 4.54(2H, s), 6.60(2H, d, J=8.0Hz), 7.22(2H, d, J=8.0Hz) |
| 6 | (thiazolidine) | 69/16 | 2.67(8H, s), 3.41(2H, s), 6.64(2H, dt, J=8.4, 1.0Hz), 7.07(2H, dt, J=8.4, 1.0Hz). |
| 7 | (thiomorpholine) | 70/34 | 2.94(dt, J=6.2, 1.6 Hz), 3.09(2H, dt, J=8.4, 1.0Hz), 7.07(2H, dt, J=8.4, 4.06(2H, s), 6.66(2H, dt, J=8.4, 1.8Hz), 7.14(2H, dt, J=8.4, 1.8 Hz). |
| 8 | (4-piperidone) | 60/69 | 2.20–2.75(8H, m), 3.40(2H, s), 6.45–6.54(2H, m), 6.91–7.00(2H, m). |

*$^1$H NMR in Reference Example 3 was measured with DMSO-d$_6$.

Reference Example 9

Preparation of 5-(4-Aminobenzyl)-2,4-oxazolidinedione

To a solution of methyl 3-(4-aminophenyl)-2-hydroxypropionate (4.50 g) and triethylamine (3.2 ml) in acetonitrile (50 ml) was added benzyloxycarbonyl chloride (5.9 ml) under ice cooling, and the mixture was stirred at room temperature for 30 minutes. The reaction mixture was poured into water and extracted with ethyl acetate, and the ethyl acetate layer was washed with an aqueous ammonium chloride solution, water, saturated sodium hydrogencarbonate aqueous solution, and saturated brine, successively, and dried (MgSO$_4$). Solvent was distilled off under reduced pressure, and the residue was purified by silica gel chromatography to give methyl 3-(4-benzyloxycarbonylaminophenyl)-2-hydroxypropionate (5.61 g, 74%). To a solution of 3-(4-benzyloxycarbonylaminophenyl)-2-hydroxypropionate (4.88 g) in tetrahydrofuran (THF)(120 ml) was added 2N potassium hydroxide aqueous solution (14 ml) under ice cooling, and the mixture was stirred at room temperature for 4 hours. The reaction mixture was acidified with conc. hydrochloric acid, extracted with ethyl acetate, and the ethyl acetate layer was washed with an aqueous ammonium chloride solution, water and saturated brine, successively, and dried (MgSO$_4$). Solvent was distilled off under reduced pressure. The precipitated crystals were washed with isopropyl ether to give 3-(4-benzyloxycarbonylaminophenyl)-2-hydroxypropionic acid (4.20 g, 90%). To a solution of 3-(4-benzyloxycarbonylaminophenyl)-2-hydroxypropionic acid (4.20 g) and triethylamine (8.3 ml) in THF (200 ml) was added ethyl chloroformate (4.3 ml) at −10° C., and the mixture was stirred at the same temperature for 1 hour. After addition of ammonia (28% water solution, 15 ml), the mixture was further stirred at room temperature for 1 hour. The reaction mixture was poured into water and extracted with ethyl acetate, and the ethyl acetate layer was washed with an aqueous ammonium chloride solution, water and saturated brine, successively, and dried (MgSO$_4$). Solvent was distilled off to give 3-(4-benzyloxycarbonylaminophenyl)-2-ethoxy-carbonyl-propanamide (5.11 g, 97%). To a solution of 3-(4-benzyloxy-carbonylaminophenyl)-2-ethoxycarbonylpropanamide (4.56 g) in acetonitrile (200 ml) was added 1,8-diazabicyclo[5.4.0]-7-undecene (DBU)(3.8 ml), and the mixture was stirred at room temperature for 12 hours. The reaction mixture was condensed under reduced pressure and dissolved in ethyl acetate. The ethyl acetate layer was washed with an aqueous ammonium chloride solution, water and saturated brine, successively, and dried (MgSO$_4$), and the solvent was distilled off under reduced pressure. The precipitated crystals were collected by filtration and washed with a mixture of isopropyl ether/hexane to give 5-(4-benzyloxycarbonylaminophenyl)methyl-2,4-oxazolidinedione (3.66 g, 84%). To a solution of 5-(4-benzyloxycarbonyl-aminophenyl)methyl-2,4-oxazolidinedione (3.46 g) in ethanol (200 ml) was added 5% palladium-carbon (0.40 g), and the mixture was stirred in hydrogen atmosphere for 30 minutes. Insoluble material was filtered off, the mother liquor was condensed under reduced pressure, and the precipitated crystals were collected by filtration and washed with a mixture of isopropyl ether/ hexane to give the title compound (2.10 g, 100%).

$^1$H-NMR (DMSO-d$_6$) δ: 2.86 (1H, dd, J=15.0, 5.4 Hz), 3.00 (1H, dd, J=15.0, 4.4 Hz), 5.12 (1H, dd, J=5.4, 4.4 Hz), 6.47 (2H, d, J=8.4 Hz), 6.83 (2H, d, J=8.4 Hz).

Reference Example 10

Preparation of 2-(4-Aminobenzyl)-3,5-dioxo-1,2,4-oxadiazolidine

To a mixture of N-hydroxy-4-nitrobenzylamine (3.03 g), acetic acid (9 ml) and water (18 ml) was dropwise added an aqueous solution (18 ml) of potassium cyanate (7.85 g), and the mixture was stirred at room temperature overnight. The reaction mixture was condensed under reduced pressure and extracted with ethyl acetate. The extract was washed with water and saturated brine, dried (MgSO$_4$), and condensed to give N-hydroxy-N-(4-nitrobenzyl)urea (2.5 g, 66%). To a solution of N-hydroxy-N-(4-nitrobenzyl)urea (2.5 g) and ethyl chloroformate (1.93 g) in THF (50 ml) and water (100 ml) was added 1N sodium hydroxide aqueous solution (35 ml), and the mixture was refluxed under heating overnight. The reaction mixture was poured into ethyl acetate, and the organic layer was collected, washed with water and saturated brine, dried (MgSO$_4$), and condensed under reduced pressure. The precipitated crystals were collected by filtration and washed with isopropyl ether to give 2-(4-nitrobenzyl)-3,5-dioxo-1,2,4-oxadiazolidine. This was dissolved in ethanol (100 ml), to which was added 5% palladium-carbon (0.3 g), and the mixture was hydrogenated in hydrogen atmosphere to give the title compound (0.63 g, 17%).

$^1$H-NMR (DMSO-d$_6$) δ: 3.34 (2H, s), 7.30 (2H, d, J=8.4 Hz), 7.75 (2H, d, J=8.4 Hz).

Reference Example 11

Preparation of 2-(4-Aminobenzyl)-1,1-dioxotetrahydro-2H-1-isothiazole

To a solution of 4-nitrobenzylamine hydrochloride (5.00 g) and triethylamine (5.37 g) in DMF (30 ml) was added 3-chloropropylsulfonyl chloride (4.69 g) under ice cooling, and the mixture was stirred at room temperature for 8 hours. The reaction mixture was then poured into water and extracted with ethyl acetate. The ethyl acetate layer was washed with water and saturated brine, dried (MgSO$_4$), and the solvent removed by distillation under reduced pressure. The residue was purified by silica gel column chromatography (ethyl acetate:hexane=1:5) to give N-(3-chloropropylsulfonyl)-4-nitrobenzylamine (2.00 g, 26%). To a solution of N-(3-chloropropylsulfonyl)-4-nitrobenzylamine (2.00 g) in THF (40 ml) was added sodium hydride (0.30 g) under ice cooling, and the mixture was stirred at room temperature for 8 hours, then poured into diluted hydrochloric acid and extracted with ethyl acetate. The ethyl acetate layer was washed with water and saturated brine, dried (MgSO$_4$), and the solvent removed by distillation under reduced pressure. The residue was purified by silica gel column chromatography (ethyl acetate:hexane= 1:1) to give 2-(4-nitrobenzyl)-1,1-dioxotetrahydro-2H-1-isothiazole (0.27 g, 15%). To a solution of 2-(4-nitrobenzyl)-1,1-dioxotetrahydro-2H-1-isothiazole (0.27 g) in ethanol (50 ml) was added 5% palladium-carbon (0.31 g), and the mixture was stirred in hydrogen atmosphere for 1.5 hours. Insoluble material was filtered off, and the mother liquor was condensed to give the title compound (0.23 g, 95%).

$^1$H-NMR (CDCl$_3$) δ: 2.28 (2H, quintet, J=7.0, 2.0 Hz), 3.08 (2H, t, J=7.0 Hz), 3.19 (2H, dd, J=8.0, 7.0 Hz), 3.71 (2H, brs), 4.06 (2H, s), 6.55 (2H, dt, J=8.2, 2.6 Hz), 7.13 (2H, dt, J=8.2, 2.6 Hz).

Reference Example 12

Preparation of 6-Hydroxy-8-methoxy-5-oxo-1,2,4,5-tetra-hydro-3-benzothiepine-2-carboxylic Acid A solution of methyl 2-bromo-3-(3,5-dimethoxyphenyl) propionate (18.3 g), potassium carbonate (9.18 g) and mercaptoacetic acid (6.12 ml) in DMF (100 ml) was stirred at room temperature for 14 hours. Insoluble material was filtered off, and the mother liquor was condensed under reduced pressure. The resulting oily material was dissolved in ethyl acetate, washed with diluted aqueous hydrochloric acid and saturated brine, dried (MgSO$_4$), and then condensed to give 2-{[1-(3,5-dimethoxybenzyl)-2-methoxy-2-oxoethyl]sulfanyl}acetic acid (18.7 g, 99%) as a colorless oil.

To a solution of 2-{[1-(3,5-dimethoxybenzyl)-2-methoxy-2-oxoethyl]sulfanyl}acetic acid (16.5 g) in trifluoroacetic acid (50 ml) was added trifluoroacetic anhydride (50 ml), and the mixture was stirred at room temperature for 2 days. The reaction mixture was condensed and then extracted with ethyl acetate, and the extract was washed with saturated aqueous sodium hydrogen carbonate solution and saturated brine, and dried (MgSO$_4$). Solvent was distilled off and the resulting residue was applied to silica gel column chromatography. Elution with ethyl acetate/n-hexane (1:2, v/v) afforded methyl 6,8-dimethoxy-5-oxo-1,2,4,5-tetrahydro-3-benzothiepine-2-carboxylate (9.5 g, 61%) as a brown oil.

To a solution of methyl 6,8-dimethoxy-5-oxo-1,2,4,5-tetrahydro-3-benzothiepine-2-carboxylate (8.5 g) in di-chloromethane (200 ml) was added boron tribromide (1M-di-chloromethane solution, 28.7 ml) under cooling at −78° C., and the mixture was stirred for 30 minutes, then poured into water and extracted with chloroform. The extract was washed with an aqueous sodium hydrogencarbonate solution, aqueous ammonium chloride solution, and saturated brine, then dried (MgSO$_4$), and evaporated. The residue was purified by silica gel column chromatography (AcOEt/n-hexane=v/v=1/3) to give methyl 6-hydroxy-8-methoxy-5-oxo-1,2,4,5-tetrahydro-3-benzothiepine-2-carboxylate as colorless crystals (3.5 g, 43%).

$^1$H-NMR (CDCl$_3$) δ: 3.18 (1H, dd, J=15.0, 5.2 Hz), 3.32–3.54 (2H, m), 3.71 (1H, dd, J=11.8, 5.2 Hz), 3.80 (3H, s), 3.84 (3H, s), 4.07–4.17 (1H, m), 6.34 (1H, d, J=2.6 Hz), 6.41 (1H, d, J=2.6 Hz).

A mixture of methyl 6-hydroxy-8-methoxy-5-oxo-1,2,4,5-tetrahydro-3-benzothiepine-2-carboxylate (1.0 g), 2N-potassium hydroxide aqueous solution (4 ml) and THF (30 ml) was stirred at 70° C. for 2 hours, then acidified with diluted hydrochloric acid, and extracted with ethyl acetate. The extract was washed with an aqueous ammonium chloride solution and saturated brine, dried (MgSO$_4$), and evaporated. The residual oily material was crystallized from ethyl acetate and isopropyl ether to give the title compound (0.78 g, 82%) as dark brown crystals.

$^1$H-NMR (CDCl$_3$) δ: 3.24–3.52 (3H, m), 3.73 (1H, dd, J=10.4, 5.6 Hz), 3.82 (3H, s), 4.11–4.20 (1H, m), 6.45 (1H, d, J=2.2 Hz), 6.53 (1H, d, J=2.2 Hz), 12.85 (1H, s).

Example 1

Preparation of (2R,4S)-N-[4-(2,4-Dioxothiazolidin-5-yl-methyl)phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.28 g), 5-(4-aminobenzyl)-2,4-dioxothiazolidine (0.233 g), 1-ethyl-3-(3-dimethylaminopropyl)carbodiimide hydrochloride (0.288 g) and 1-hydroxybenzotriazole (HOBt)(0.162 g) in N,N-dimethylformamide (DMF)(10 ml) was stirred at room temperature for 14 hours. The reaction mixture was diluted with chloroform (50 ml), washed with a saturated sodium hydrogen carbonate aqueous solution, water, 1N-hydrochloric acid, water, and saturated brine, successively, then dried (MgSO$_4$), and the solvent was distilled off. The residue was purified by silica gel column chromatography, and the resulting colorless oil was treated with isopropyl ether to give colorless crystals, which were washed with ethyl acetate/isopropyl ether to give the title compound (0.47 g, 47%). mp. 139–144° C.

Example 2

Preparation of (2R,4S)-N-[4-(Hydantoin-3-ylmethyl)phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.40 g), 3-(4-aminobenzyl)hydantoin (0.233 g), 1-ethyl-3-(3-dimethylaminopropyl)carbodiimide hydrochloride (0.288 g) and HOBt(0.162 g) in DMF (10 ml) was stirred at room temperature for 14 hours. The reaction mixture was diluted with chloroform (50 ml), washed with a saturated sodium hydrogen carbonate aqueous solution, water, 1N-hydrochloric acid, water, and saturated brine, successively, then dried (MgSO$_4$), and the solvent was distilled off. The residue was purified by silica gel column chromatography, and the resulting colorless oil was treated with isopropyl ether to give colorless crystals, which were washed with ethyl acetate/isopropyl ether to give the title compound (0.47 g, 47%). mp. 139–144° C.

Example 3

Preparation of (2R,4S)-N-[4-(2,4-Dioxothiazolidin-3-yl-methyl)phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.589 g), 3-(4-aminobenzyl)-2,4-dioxothiazolidine (0.470 g), 1-ethyl-3-(3-dimethylaminopropyl)carbodiimide hydrochloride (0.805 g) and HOBt(0.426 g) in DMF (30 ml) was stirred at room temperature for 14 hours, then poured into water (50 ml), and extracted with ethyl acetate. The ethyl acetate layer was washed with 1N-hydrochloric acid, water, saturated sodium hydrogencarbonate aqueous solution, water, and saturated brine, successively, and dried (MgSO$_4$). The solvent was distilled off, and the residual crystals were collected by filtration and washed with hexane/isopropyl ether to give the title compound (0.88 g, 86%). mp. 232–235° C.

Example 4

Preparation of (2R,4S)-N-[4-(4-Morpholinylmethyl)phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.400 g), 4-(4-aminobenzyl)morpholine (0.290 g), 1-ethyl-3-(3-dimethylaminopropyl)carbodiimide hydrochloride (0.550 g) and HOBt(0.290 g) in DMF (15 ml) was stirred at room temperature for 14 hours, then poured into water (50 ml), and extracted with ethyl acetate. The ethyl acetate layer was washed with a saturated sodium hydrogencarbonate aqueous solution, water, and saturated brine, successively, and dried (MgSO$_4$). The solvent was distilled off, and the residual crystals were collected by filtration and washed with hexane/isopropyl ether to give the title compound (0.55 g, 85%). mp. 172–174° C.

Example 5

Preparation of (2R,4S)-N-[4-(2,6-Dioxo-1-piperidinyl-methyl)phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.330 g), 1-(4-aminobenzyl)glutarimide (0.300 g), 1-ethyl-3-(3-dimethylaminopropyl)carbodiimide hydrochloride (0.52 g) and HOBt(0.240 g) in DMF (20 ml) was stirred at room temperature for 14 hours, then poured into water (50 ml), and extracted with ethyl acetate. The ethyl acetate layer was washed with 1N-hydrochloric acid, water, saturated sodium hydrogencarbonate aqueous solution, water, and saturated brine, successively, and dried (MgSO$_4$). The solvent was distilled off, and the. residual crystals were collected by filtration and washed with isopropyl ether to give the title compound (0.465 g, 82%). mp. 205–208° C.

Example 6

Preparation of (2R,4S)-N-[4-(1-Methylhydantoin-3-ylmethyl)-phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2- carboxylic acid (0.302 g), 3-(4-aminobenzyl)-1-methylhydantoin (0.213 g), 1-ethyl-3-(3-dimethylaminopropyl)carbodiimide hydrochloride (0.228 g) and HOBt(0.160 g) in DMF (6 ml) was stirred at room temperature for 14 hours, then poured into water (50 ml), and extracted with ethyl acetate. The ethyl acetate layer was washed with 1N-hydrochloric acid, water, saturated sodium hydrogencarbonate aqueous solution, water, and saturated brine, successively, and dried (MgSO$_4$). The solvent was distilled off, and the residual crystals were collected by filtration and washed with isopropyl ether to give the title compound (0.42 g, 81%). mp. 228–230° C.

Example 7

Preparation of (2R,4S)-N-[4-(2,4-Dioxo-oxazolidin-3-yl-methyl)phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.320 g), 1-(4-aminobenzyl)-2,4-dioxo-oxazolidine (0.215 g), 1-ethyl-3-(3-dimethylaminopropyl)carbodiimide hydrochloride (0.239 g) and HOBt(0.169 g) in DMF (20 ml) was stirred at room temperature for 14 hours, and then poured into water (50 ml). The precipitated crystals were washed with water, saturated sodium hydrogencarbonate, water, cold ethanol and isopropyl ether, successively, to give the title compound (0.380 g, 78%). mp. 240–242° C.

Example 8

Preparation of (2R,4S)-N-[4-(Succinimdomethyl) phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.70 g), 1-(4-aminobenzyl)succinimide (0.51 g), 1-ethyl-3-(3-dimethylaminopropyl)carbodiimide hydrochloride (0.37 g) and HOBt(0.58 g) in DMF (20 ml) was stirred at room temperature for 14 hours, and then poured into water (50 ml). The precipitated crystals were washed with water, saturated sodium hydrogencarbonate, water, cold ethanol and isopropyl ether, successively, and collected by filtration. Recrys-tallization from chloroform/ethanol afforded the title compound (0.93 g, 80%). mp. 232–2330° C.

Example 9

Preparation of (2R,4S)-N-[4-(2-Oxazolidon-3-ylmethyl)-phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.400 g), 3-(4-aminobenzyl)-2-oxazolidone (0.279 g), 1-ethyl-3-(3-dimethylaminopropyl)carbodiimide hydrochloride (0.307 g) and HOBt(0.217 g) in DMF (6 ml) was stirred at room temperature for 14 hours, then poured into water (50 ml), and extracted with ethyl acetate. The ethyl acetate layer was washed with a saturated sodium hydrogencarbonate aqueous solution, water, and saturated brine, successively, and dried (MgSO$_4$). The solvent was distilled off, and the residual crystals were collected by filtration and recrystallized from tetrahydrofuran (THF)/ethyl acetate to give the title compound (0.25 g, 38%). mp. 231–233° C.

Example 10

Preparation of (2R,4S)-N-[4-(2,4-Dioxo-oxazolidin-5-yl-methyl)phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.400 g), 5-(4-aminobenzyl)-2,4-dioso-oxazolidine (0.300 g), 1-ethyl-3-(3-dimethylaminopropyl) carbodiimide hydrochloride (0.550 g) and HOBt(0.290 g) in DMF (20 ml) was stirred at room temperature for 14 hours, then poured into water (50 ml), and extracted with ethyl acetate. The ethyl acetate layer was washed with 1N-hydrochloric acid, water, saturated sodium hydrogencarbonate aqueous solution, water, and saturated brine, successively, and dried (MgSO$_4$). The solvent was distilled off, and the residual crystals were collected by filtration and washed with isopropyl ether to give the title compound (0.636 g, 95%). mp. 164–166° C.

Example 11

Preparation of (2R,4S)-N-[4-(3,5-Dioxo-1,2,4-oxadiazolidin-2-ylmethyl)phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.28 g), 2-(4-aminobenzyl)-3,5-dioxo-1,2,4-oxadi-azolidine (0.200 g), 1-ethyl-3-(3-dimethylaminopropyl)-carbodiimide hydrochloride (0.228 g) and HOBt(0.141 g) in DMF (6 ml) was stirred at room temperature for 16 hours, then poured into water (50 ml), and extracted with ethyl acetate. The ethyl acetate layer was washed with a saturated sodium hydrogen carbonate aqueous solution, water, and saturated brine, successively, and dried (MgSO$_4$). The solvent was distilled off, and the residual crystals were collected by filtration and recrystallized from THF/ethyl acetate to give the title compound (0.26 g, 57%). mp. 237–239° C.

Example 12

Preparation of (2R,4S)-N-[4-(1,1-Dioxotetrahydro-2H-1-iso-thiazol-2-ylmethyl)phenyl]-1,2,4,5-tetrahydro-7,8-methyl-enedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.28 g), 2-(4-aminobenzyl)-1,1-dioxotetrahydro-2H-1-isothiazole (0.210 g), 1-ethyl-3-(3-dimethylaminopropyl)-carbodiimide hydrochloride (0.207 g) and HOBt(0.141 g) in DMF (10 ml) was stirred at room temperature for 14 hours, then poured into water (50 ml), and extracted with ethyl acetate. The ethyl acetate layer was washed with a saturated sodium hydrogen carbonate aqueous solution, water, and saturated brine, successively, and dried (MgSO$_4$). The solvent was distilled off, and the residual crystals were collected by filtration and recrystallized from ethyl acetate/hexane to give the title compound (0.29 g, 66%). mp. 215–217° C.

Example 13

Preparation of (2R,4S)-N-[4-(1-Pyrrolidinylmethyl) phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.28 g), 1-(4-aminobenzyl)pyrrolidine (0.194 g), 1-ethyl-3-(3-dimethylaminopropyl)carbodiimide hydrochloride (0.383 g) and HOBt(0.203 g) in DMF (10 ml) was stirred at room temperature for 14 hours, then poured into water (50 ml), and extracted with ethyl acetate. The ethyl acetate layer was washed with a saturated sodium hydrogencarbonate aqueous solution, water, and saturated brine, successively, and dried ($MgSO_4$). The solvent was distilled off, and the residual crystals were collected by filtration and washed with isopropyl ether to give the title compound (0.29 g, 66%). mp. 186–188° C.

Example 14

Preparation of (2R,4S)-N-[4-(1-Piperidinylmethyl) phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.28 g), 1-(4-aminobenzyl)piperidine (0.190 g), 1-ethyl-3-(3-dimethylaminopropyl)carbodiimide hydrochloride (0.383 g) and HOBt(0.203 g) in DMF (15 ml) was stirred at room temperature for 14 hours, then poured into water (50 ml), and extracted with ethyl acetate. The ethyl acetate layer was washed with a saturated sodium hydrogencarbonate aqueous solution, water, and saturated brine, successively, and dried ($MgSO_4$). The solvent was distilled off, and the residual crystals were collected by filtration and washed with isopropyl ether to give the title compound (0.38 g, 83%). mp. 162–165° C.

Example 15

Preparation of (2R,4S)-N-Methyl-N-[4-(4-morpholinylmethyl)-phenyl]-1,2,4,5-tetrahydro-7,8-methylenedioxy-4-methyl-5-oxo-3-benzothiepine-2-carboxamide To a solution of (2R,4S)-(−)-1,2,4,5-tetrahydro-7,8-methylenedioxy-4-methyl-5-oxo-3-benzothiepine-2-carboxylic acid (0.281 g) and DMF (3 drops) in tetrahydrofuran (THF)(10 ml) was added oxalyl chloride (0.13 ml) under ice cooling, and the mixture was stirred for 1 hours, and then condensed under under reduced pressure. The residue was dissolved in THF (10 ml), to which was added 4-(4-methylaminobenzyl)morpholine (0.203 g) and triethylamine (0.28 ml), and the mixture was stirred at room temperature for 3 hours, then poured into water, and extracted with ethyl acetate. The ethyl acetate layer was washed with a saturated sodium hydrogencarbonate aqueous solution, water, and saturated brine, successively, and dried ($MgSO_4$). The solvent was distilled off, and the residue was applied to silica gel column chromatography and eluted with chloroform/ethyl acetate/methanol (10:10:1, v/v/v) to give the title compound (0.42 g, 89%). mp. 162–165° C.

Example 16

Preparation of (2R,4S)-N-[4-(1,3-Thiazolidin-3-ylmethyl)-phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.433 g), 1-(4-aminobenzyl)thiazolidine (0.295 g), 1-ethyl-3-(3-dimethylaminopropyl)carbodiimide hydrochloride (0.305 g) and HOBt(0.21 g) in DMF (6 ml) was stirred at room temperature for 24 hours, then poured into water (50 ml), and extracted with ethyl acetate. The ethyl acetate layer was washed with a saturated sodium hydrogencarbonate aqueous solution, water, and saturated brine, successively, and dried ($MgSO_4$). The solvent was distilled off, and the residual crystals were collected by filtration and recrystallized from tetrahydrofuran/isopropyl ether to give the title compound (0.41 g, 59%). mp. 179–181° C.

Example 17

Preparation of (2R,4S)-N-[4-(4-Thiomorpholinylmethyl)-phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.405 g), 1-(4-aminobenzyl) thiomorpholine (0.313 g), 1-ethyl-3-(3-dimethylaminopropyl)carbodiimide hydrochloride (0.307 g) and HOBt(0.21 g) in DMF (12 ml) was stirred at room temperature for 16 hours, then poured into water (50 ml), and extracted with ethyl acetate. The ethyl acetate layer was washed with a saturated sodium hydrogencarbonate aqueous solution, water, and saturated brine, successively, and dried ($MgSO_4$). The solvent was distilled off, and the residual crystals were collected by filtration and recrystallized from ethyl acetate/isopropyl ether to give the title compound (0.44 g, 65%). mp. 204–206° C.

Example 18

Preparation of (2R,4S)-N-[4-(4-Oxo-1-piperidinylmethyl)-phenyl]-1,2,4,5-tetrahydro-7,8-methylenedioxy-4-methyl-5-oxo-3-benzothiepine-2-carboxamide A solution of (2R,4S)-(−)-1,2,4,5-tetrahydro-7,8-methylenedioxy-4-methyl-5-oxo-3-benzothiepine-2-carboxylic acid (0.433 g), 1-(4-aminobenzyl)-4-oxopiperidine (0.39 g), 1-ethyl-3-(3-dimethylaminopropyl) carbodiimide hydrochloride (0.37 g) and HOBt(0.26 g) in DMF (10 ml) was stirred at room temperature for 14 hours, then poured into water (50 ml), and extracted with ethyl acetate. The ethyl acetate layer was washed with a saturated sodium hydrogencarbonate aqueous solution, water, and saturated brine, successively, and dried ($MgSO_4$). The solvent was distilled off, and the residual crystals were collected by filtration and recrystallized from ethyl acetate/hexane to give the title compound (0.19 g, 23%). mp. 199–201° C.

The structural formulae of the compounds obtained in the above Examples 1–18 are shown in the following Table 2.

TABLE 2
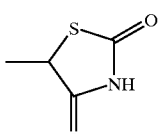
| Example No. | R² | R¹ |
|---|---|---|
| 1 | H | 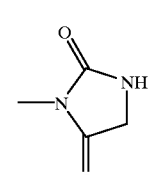 |
| 2 | H | 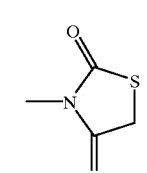 |
| 3 | H | 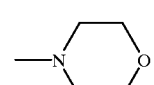 |
| 4 | H | 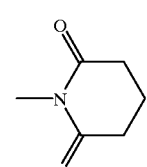 |
| 5 | H | 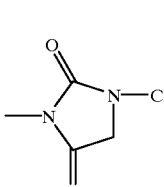 |
| 6 | H | 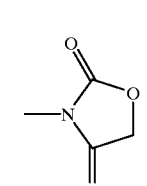 |
| 7 | H | 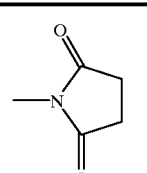 |
TABLE 2-continued
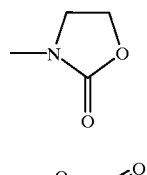
| Example No. | R² | R¹ |
|---|---|---|
| 8 | H | 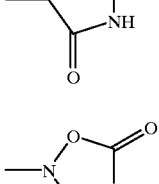 |
| 9 | H | 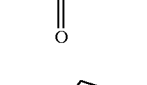 |
| 10 | H | 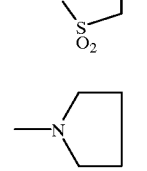 |
| 11 | H | 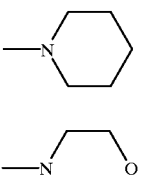 |
| 12 | H | 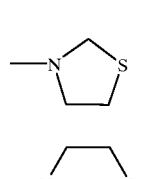 |
| 13 | H | 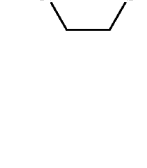 |
| 14 | H | |
| 15 | CH₃ | |
| 16 | H | |
| 17 | H | |

TABLE 2-continued

| Example No. | R² | R¹ |
|---|---|---|
| 18 | H | (piperidinyl with =O) |

Example 19

Preparation of N-[4-[(2,4-Dioxo-1,3-thiazolidin-5-yl)-methyl]phenyl]-6-hydroxy-8-methoxy-5-oxo-1,2,4,5-tetrahydro-3-benzothiepine-2-carboxamide To a solution of 6-hydroxy-8-methoxy-5-oxo-1,2,4,5-tetrahydro-3-benzothiepine-2-carboxylic acid (0.134 g), 5-(4-aminobenzyl)-2,4-dioxo-1,3-thiazolidine (0.12 g), and 1-ethyl-3-(3-dimethylaminopropyl)carbodiimide hydrochloride (0.192 g) in DMF (5 ml) was added 1-hydroxybenzotriazole (HOBt) (0.10 g), and the mixture was stirred at room temperature for 14 hours, then poured into water, and extracted with a mixture of ethyl acetate and THF. The extract was washed with a sodium hydrogencarbonate aqueous solution, aqueous ammonium chloride solution, and saturated brine, dried (MgSO$_4$), and evaporated to give the objective compound (0.16 g, 69%). mp. 131–134° C.

Example 20

The compound (10 mg) prepared in Example 1, lactose (90 mg), fine crystalline cellulose (70 mg) and magnesium stearate (5 mg) are mixed and formulated into granules. Magnesium stearate (5 mg) is added thereto, and the whole is included in a gelatin capsule.

Example 21

The compound (10 mg) prepared in Example 4, lactose (35 mg), corn starch (150 mg), fine crystalline cellulose (20 mg) and magnesium stearate (2.5 mg) are mixed and formulated into granules. Fine crystalline cellulose (10 mg) and magnesium stearate (2.5 mg) are added to the granules, mixed and formulated into a tablet under pressure.

Example 22

The compound (10 mg) prepared in Example 10, inositol (100 mg) and benzyl alcohol (20 mg) are dissolved in distilled water for injection so that the whole volume becomes 2 ml, and placed in an ampoule. All operations are carried out under a sterilized condition.

Example 23

The compound (10 mg) prepared in Example 11, lactose (35 mg), corn starch (150 mg), fine crystalline cellulose (20 mg) and magnesium stearate (2.5 mg) are mixed and formulated into granules. Fine crystalline cellulose (10 mg) and magnesium stearate (2.5 mg) are added to the granules, mixed and formulated into a tablet under pressure.

Test Example 1

Osteogenesis Promoting Effect

Using the interstitial cells prepared from the femur bone marrow of a normal rat, an alkaline phosphatase activity was measured as an index of osteogenesis. Briefly, according to the method of Maniatopoulos et al. [Cell Tissue Research, volume 254, P.317 (1988)], the interstitial cells were prepared from the femur bone of a Sprague-Dawley male rat, 7 weeks of age, and cultured in an α-MEM (minimum essential medium) solution containing dexamethasone ($10^{-7}$M) and β-glycerophosphoric acid ($10^{-2}$M) in order to generate calcified bony tissue. One week later, the confluent primary cells were treated with 0.25% trypsin-0.2% EDTA solution, recovered, and subcultured on a culture plate at a cell density of $1.6 \times 10^{-4}$ cells/cm², (culture day 0). From the 2nd day of the culture, a test compound ($10^{-5}$ M) was added to the above culture solution, and cultured for additional 5 days. The cells were washed with a phosphate buffer, and after addition of 0.2% Nonidet P-40, they were homogenized and centrifuged at 3,000 rpm for 10 minutes. The supernatant was measured for an alkaline phosphatase activity according to the method of Lowry et al. [Journal of Biological Chemistry, volume 207, P.19 (1954)]. Table 3 shows the measured values in terms of mean±standard error (SE). Statistical analysis was performed by means of the Student's t-test.

TABLE 3

| Compound | Concentration (M) | Alkaline phosphatase activity (A$_{405}$) |
|---|---|---|
| Example no. 1 | $10^{-5}$ | 0.489 ± 0.050** |
| Example no. 4 | $10^{-5}$ | 0.394 ± 0.036** |
| Example no. 10 | $10^{-5}$ | 0.535 ± 0.069** |
| Example no. 11 | $10^{-5}$ | 0.399 ± 0.069** |
| Control | No addition | 0.150 ± 0.009 |

Mean ± S.E. (n = 4),
**p < 0.01 vs control (Student's t-test)

From Table 3, it is found that the test compounds have an excellent osteogenesis promoting effect.

INDUSTRIAL APPLICABILITY

The compounds of the invention and salts thereof have a potent osteogenesis promoting effect, chondrogenesis promoting effect, cartilage destruction suppressing effect, and cartilage cell differentiation induction promoting effect, and are superior in clinically useful characteristics such as stability, absorption (particularly, oral absorption), bioavailability, and the like. They, accordingly, can be used in prevention and treatment of bone diseases or chondropathy, for example, osteoporosis, fracture, cartilage defect, chronic rheumatoid arthritis involving a cartilage, and osteoarthritis involving a cartilage.

What is claimed is:

1. A compound of the formula:

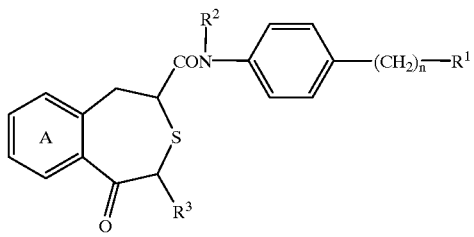

wherein the ring A is an optionally substituted benzene ring; $R^1$ is an optionally substituted non-aromatic heterocyclic group; $R^2$ and $R^3$ are independently hydrogen atom or an optionally substituted hydrocarbon group; n is an integer of 0–3; or a salt thereof.

2. A compound according to claim 1,
wherein the ring A is a benzene ring which may be substituted by 1 or 2 substituents selected from the group consisting of
halogen atom,
hydroxy,
$C_{1-10}$ alkyl,
$C_{1-10}$ alkoxy,
alkylenedioxy of the formula: $-O-(CH_2)_m-O-$; wherein m is an integer of 1–4, and $C_{1-10}$ alkylthio; and
$R^2$ and $R^3$ are independently hydrogen atom, $C_{1-6}$ alkyl or phenyl.

3. A compound according to claim 1, wherein the ring A is a group of the formula:

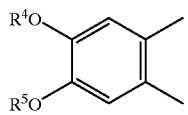

wherein $R^4$ and $R^5$ are independently hydrogen atom or $C_{1-10}$ alkyl or $R^4$ and $R^5$ may be bound to each other to form a $C_{1-4}$ alkylene chain; and $R^2$ and $R^3$ are independently hydrogen atom or $C_{1-6}$ alkyl.

4. A compound according to claim 1, wherein the non-aromatic heterocyclic group of the optionally substituted non-aromatic heterocyclic group represented by $R^1$ is a 5- to 6-membered non-aromatic heterocyclic group containing from 1 to 4 heteroatoms selected from the group consisting of nitrogen atom, sulfur atom and oxygen atom.

5. A compound according to claim 4, wherein the 5- to 6-membered non-aromatic heterocyclic group is one containing at least 1 nitrogen atom.

6. A compound according to claim 5, wherein the heterocycle of the 5- to 6-membered non-aromatic heterocyclic group is pyrrolidine, imidazolidine, thiazolidine, isothiazolidine, oxazolidine, oxadiazolidine, piperidine, piperazine, thiomorpholine or morpholine.

7. A compound according to claim 1, wherein the substituent or substituents in the optionally substituted non-aromatic heterocyclic group represented by $R^1$ are 1 to 3 substituents selected from the group consisting of halogen atom, hydroxy or oxo, $C_{1-10}$ alkyl, $C_{1-6}$ alkoxy, $C_{1-6}$ acyl, amino, mono- or di-$C_{1-6}$ alkylamino, $C_{1-6}$ alkylsulfonyl, carboxy and $C_{1-6}$ alkoxy-carbonyl.

8. A compound according to claim 3, wherein $R^2$ is a hydrogen atom; $R^3$ is $C_{1-3}$ alkyl; and $R^4$ and $R^5$ may be bound to each other to form a $C_{1-2}$ alkylene chain.

9. A compound according to claim 3, wherein $R^2$ and $R^3$ are independently a hydrogen atom, and $R^4$ and $R^5$ are independently a $C_{1-3}$ alkyl group.

10. N-[4-(4-Morpholinylmethyl)phenyl]-1,2,4,5-tetrahydro-7,8-methylenedioxy-4-methyl-5-oxo-3-benzothiepine-2-carboxamide, N-[4-(2,4-dioxothiazolidin-5-ylmethyl)-phenyl]-1,2,4,5-tetrahydro-7,8-methylenedioxy-4-methyl-5-oxo-3-benzothiepine-2-carboxamide, or N-[4-(2,4-dioxo-oxazolidin-5-ylmethyl)phenyl]-1,2,4,5-tetrahydro-7,8-methylenedioxy-4-methyl-5-oxo-3-benzothiepine-2-carboxamide, or a salt thereof.

11. A process for producing a compound of the formula:

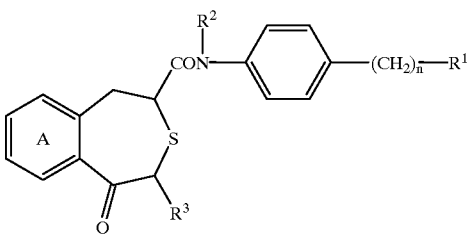

wherein the ring A is an optionally substituted benzene ring; $R^1$ is an optionally substituted non-aromatic heterocyclic group; $R^2$ and $R^3$ are independently a hydrogen atom or an optionally substituted hydrocarbon group; and n is an integer of 0–3; or a salt thereof, which comprises reacting a compound of the formula:

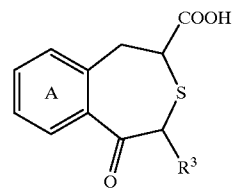

wherein each symbol has the same meanings as mentioned above; or a reactive derivative at the carboxy group thereof or a salt thereof, with a compound of the formula:

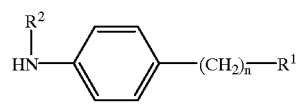

wherein each symbol has the same meanings as mentioned above; or a reactive derivative at the amino group thereof or a salt thereof.

12. A prodrug of the compound according to claim 1, or a salt thereof.

13. A pharmaceutical composition comprising a compound of the formula:
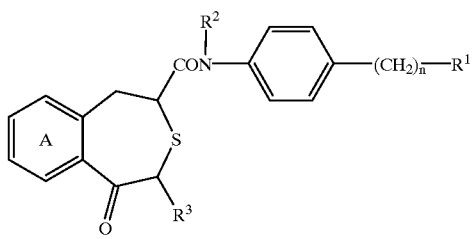
wherein
the ring A is an optionally substituted benzene ring;
$R^1$ is an optionally substituted non-aromatic heterocyclic group;
$R^2$ and $R^3$ are independently hydrogen atom or an optionally substituted hydrocarbon group;
and n is an integer of 0–3;
or a salt thereof;
and a pharmaceutically acceptable carrier.
* * * * *